United States Patent
Hintermann et al.

(10) Patent No.: US 6,472,345 B2
(45) Date of Patent: Oct. 29, 2002

(54) CATALYTIC HALOGENATION OF ACTIVATED METHYLENE AND METHINE COMPOUNDS

(75) Inventors: Lukas Hintermann, Tokyo (JP); Antonio Togni, Russikon (CH)

(73) Assignee: Solvias AG, Basel (CH)

( * ) Notice: Subject to any disclaimer, the term of this patent is extended or adjusted under 35 U.S.C. 154(b) by 0 days.

(21) Appl. No.: 09/846,318

(22) Filed: May 2, 2001

(65) Prior Publication Data

US 2002/0026067 A1 Feb. 28, 2002

(30) Foreign Application Priority Data

May 3, 2000 (CH) .............................................. 0861/00

(51) Int. Cl.$^7$ ........................ B01J 27/135; C07C 255/04
(52) U.S. Cl. ........................................ 502/227; 558/303
(58) Field of Search ........................... 558/303; 503/227

(56) References Cited

PUBLICATIONS

Sasson, Y. "Formation of carbon–halogen bonds (Cl, Br, I)", Chapter 11 of Supplement D2: The chemistry of halides, pseudo–halides and azidies, edited by S. Patai and Z. Rappoport, ©1995 by John Wiley and Sons Ltd.
Middleton, W.J. "Adventures of a fluorine chemist at DuPont", Journal of Fluorine Chemistry, vol. 100 (1999), pp. 207–216.
Furin, G.G. "Introduction of Fluorine by N–F Compounds", Houben–Weyl, vol. E10 (1999), pp. 432–499.
Seebach, D., et al. "Dichlorol[TADDOLato(2–)–O,O ]titanium/Dichlorobis[1–methylethoxy]titanum–Mediated, Highly Diastereo– and Enantioselective Additions of Silyl Enol Ethers to Nitro Olefins and [3+2] Cycloadditions of Primary Adducts to Atceylenes", Helvetica Chimica Acta, vol. 82 (1999), pp. 1829–1841.
Seebach, D. et al. "On the Ti–TADDOLate–Catalyzed Diels–Alder Addition of 3–Butenoyl–1, 3–oxazolidin–2–one to Cyclopentadience. Genaral Features of Ti–BINOLate– and Ti–TADDOlate–Mediated Reactions", J. Org. Chem., vol. 60, No. 6 (1995), pp. 1788–1799.
Umemoto, T., et al. "Power and Structure–Variable Fluorinating Agents. The N–Fluoropyridinium Salt System", J. Am. Chem. Soc., vol. 112 (1990), pp. 8563–8575.
Chambers, R.D., et al. "Elemental Fluorine. Part 9: Catalysis of the direct fluorination of 2–Substituted carbonyl compounds", Jounral of Fluorine Chemistry, vol. 92 (1988) pp. 45–52.
Stavber, S., et al. "High Yield Direct Fluorofunctionalization of Ketones Using Accufluor™–NFTh Fluorinating Reagent", Tetrahedron Letters, vol. 37, No. 20 (1996), pp. 3591–3594.
Rozen, S. "Selective Fluorinations by Reagents Containing the OF Group", Chem. Rev., vol. 96 (1996), pp. 1717–1736.
Davis, F.A., et al. "Synthesis of α–Fluoro Aldehydes and Ketones. A Review", Organic Preparations and Procedures Int., vol. 31, No. 2 (1999), pp. 125–143.
Davis, F.A., et al. "Asymmetric Fluorination of Enolates with Nonracemic N–Fluoro–2, 10–Camphorsultans", J. Org. Chem., vol. 63 (1998), pp. 2273–2280.
Takeuchi, Y., et al. "N–Fluoro–3–cyclohexyl–3–methyl–2, 3–dihydrobenzol[1,2–d]isothiazole 1,1–Dioxide: An Efficient Agent for Electrophilic Asymmetric Fluorination of Enolates", J. Org. Chem., vol. 64 (1999), pp. 5708–5711.
Poss, A.J., et al. "1–Fluoro–4–hydroxy–1,4–diazoniabicyclo [2.2.2]octane Bis(tetrafluoroborate): An Electrophilic Fluorinating Agent", Tetrahedron Letters, vol. 40 (1999), pp. 2673–2676.
Umemoto, T., et al. "Synthesis, Properties, and Reactivity of N,N'–Difluorobipyridinium and Related Salts and Their Applications as Reactive and Easy–To–Handle Electrophilic Fluorinating Agents with High Effective Fluorine Content", J. Org. Chem., vol. 63 (1998))pp. 3379–3385.
Davis, F.A., et al. "Selective, Electrophilic Fluorinations Using N–Fluoro–o–benzenedisulfonimide", J. Org. Chem., vol. 60 (1995) pp. 4730–4737.
Banks, R.E., et al. "Efficient Electrophilic Fluorination of β–Dicarbonyl Compounds with the Selectfluor Reagent F–TEDA–BF$_4$ {1–Chloromethl–4–fluoro–1,4–diazoniabicyclo[2.2.2]octane bis(tetrafluoroborate)}", J. Chem. Soc., Chem. Commun., 1994, pp. 343–344.
Umemoto, T., et al. "Highly Selective Fluorinating Agents: A Counteranion–Bound N–Fluoropyridinium Salt System", J. Org. Chem, vol. 60 (1995), pp. 6563–6570.

*Primary Examiner*—Joseph K. McKane
*Assistant Examiner*—Kamal Saeed
(74) *Attorney, Agent, or Firm*—Wenderoth, Lind & Ponack, L.L.P.

(57) ABSTRACT

A process for the halogenation of activated methylene and methine compounds with at least equimolar amounts of an electrophilic halogenation reagent, which comprises reacting said activated methylene and methine compounds in the presence of catalytic amounts of a titanium compound of the formula I or of a titanium compound of the formula II $$R_1TiX_1X_2X_3 \qquad (I),$$

$$R_2R_3TiX_1X_2 \qquad (II),$$

in which
$R_1$ is chlorine, bromine or iodine, a substituted or unsubstituted cyclopentadienyl or indenyl, and $X_1$, $X_2$ and $X_3$ are, independently of one another, chlorine, bromine or iodine, or $X_1$, $X_2$ and $X_3$ are an organic sulfonate group where $R_1$ is a substituted or unsubstituted cyclopentadienyl or indenyl;

$R_2$ and $R_3$ are a substituted or unsubstituted cyclopentadienyl or indenyl, $R_2$ and $R_3$ together are a substituted or unsubstituted and bridged or unbridged biscyclopentadienyl or bisindenyl, or $R_2$ and $R_3$ together are a substituted or unsubstituted 1,3-, 1,4- or 1,5-diolate, and $X_1$, and $X_2$ are, independently of one another, chlorine, bromine or iodine or an organic sulfonate group.

If the diolate is enantiopure, the process is enantioselective on use of racemic activated methine compounds.

23 Claims, No Drawings

CATALYTIC HALOGENATION OF ACTIVATED METHYLENE AND METHINE COMPOUNDS

The present invention relates to a process for the halogenation of activated methylene or methine groups of organic compounds with electrophilic halogenating reagents, in which said organic compounds are reacted in the presence of catalytic amounts of a titanium tetrahalide or of an alcoholate-containing titanium(IV) trihalide or titanium (IV) dihalide with an electrophilic halogenating reagent; to a process for the enantioselective halogenation of an activated methine group of organic compounds with electrophilic halogenating reagents, in which said organic compounds are reacted in the presence of catalytic amounts of a chiral 1,3-, 1,4- or 1,5-diolate-containing titanium(IV) dihalide with a halogenating reagent.

Fluorine-substituted organic compounds have recently attracted increased interest as active pharmaceutical ingredients and pesticides. The fluorination frequently employs electrophilic fluorination reagents with which it is possible to replace hydrogen atoms in aromatic, olefinically unsaturated or activated aliphatic intermediates or final products. Large numbers of electrophilic fluorination reagents are known. Besides fluorine, those most frequently used are mainly inert gas fluorides, oxyfluorides, N-fluorinated pyridinium salts, tertiary N-fluoroammonium salts and N-fluorinated imides. A review of fluorination reagents is to be found, for example, in Chem. Rev. 1996, 96,1717–1736 by S. Rozen, and in Chem. Rev. 1996, 96, 1737 to 1755 by G. Sanker Lal et al.

The fluorination of carbon acids is generally known and is described, for example, in review articles in Houben-Weyl, 1999, volume E 10a, pages 433 to 499, by S. D. Taylor in Tetrahedron 55,1999, pages 12431 to 12477, and by F. A. Davis in Organic Preparations and Procedures Int., 1999, 31(2), pages 125–143. The fluorination is usually carried out with previous formation of carbanions or enolates by adding alkali metal amides or other strong bases.

Direct fluorinations of keto compounds have also been reported recently. T. Umemoto et al. describe in J. Org. Chem. 1995, 60, pages 6563 to 6570 the fluorination of β-diketo compounds with N-fluoro-4,6-trifluoromethylpyridinium-3-sulfonic acid, which is referred to as very reactive, at room temperature, the desired compounds being obtained usually in good yields with relatively long reaction times. To reduce the reaction times, bis-(trifluoromethyl)methanol is proposed as solvent, but a mixture of mono- and difluorinated products is formed on use thereof. R. E. Banks et al. propose in J. Chem. Soc., chem. Commun. 1994, pages 343 to 344 the use of 1-chloromethyl-4-fluoro 1,4-diazoniabicyclo[2,2,2]octane bistetrafluoroborate for the fluorination of compounds with a β-diketo structure, although the long reaction times make industrial use uneconomic. F. A. Davis et al. disclose in J. Org. Chem. 1995, 60, pages 4730 to 4737 the direct fluorination of β-diketo compounds with N-fluorobenzenedisulfonimide at room temperature, there always being formation of mixtures of mono- and difluorinated products, and it being necessary to add water for predominant formation of monofluoro products. S. Stavber et al. describe in Teterahedron Letters, Vol. 37, No. 20, 1996, pages 3591 to 3594 the use of 1-hydroxy-4-fluoro-1,4-diazoniabicyclo[2,2,2]octane bistetrafluoroborate for the fluorination of ketones at 80° C. Finally, T. Umemoto et al. describe, in J. Org. Chem. 1998, 63, pages 3379–3385, the use of N,N'-difluoro-2,2'-bipyridinium bistetrafluoroboate for the fluorination of compounds with a β-diketo structure in acetonitrile, with relatively long reaction times being necessary despite the reflux temperature.

It is also known that optical induction is possible on α-fluorination of ketones when the preformed enolates thereof are reacted with enantiopure N-fluorosultams, see, for example, E. Differding et al., Tetrahedron Letters, Vol. 29, No. 47, 1988, pages 6087 to 6090, Y. Takeuchi et al., J. Org. Chem. 1999, 64, pages 5708 to 5711, and F. A. Davis et al., J. Org. Chem. 1998, 63, pages 2273 to 2280.

T. Umemoto et al. describe, in J. Am. Chem. Soc. 1990, 112, pages 8563 to 8575, the addition of 0.4 equivalent of $ZnCl_2$ or $AlCl_3$ in the fluorination of activated methylene compounds with N-fluoro-2,4,6-trimethylpyridinium triflate. The reaction is carried out at elevated temperatures and the reaction times are relatively long despite this. Moreover mixtures of mono- and difluorinated compounds are formed. A. J. Poss et al. use 0.4 equivalent of $ZnCl_2$ together with 0.4 equivalent of imidazole in the fluorination of ethyl cyclopentanonecarboxylate and 1,3-diphenyl-1,3-propanedione (see Tetrahedron Letters 40 (1999) pages 2673 to 2676). The reaction times are long and, in addition, elevated temperature is used, and difluorination cannot be suppressed.

R. D. Chambers et al. describe in Journal of Fluorine Chemistry 92 (1998), pages 45 to 52, the fluorination of activated methylene compounds with elemental fluorine in the presence of catalytic amounts of selected metal salts such as, for example, Cu, Ni, Cr, Mn, Fe, Co and Zn dinitrate, Cu dichloride, diacetate and sulfate. The yields which can be achieved are unsatisfactory, and a large proportion of difluorinated compounds is observed on fluorination of methylene groups.

Possibilities for the chorination, bromination and iodination of organic compounds, for example ketones, are described in "The Chemistry of Functional Groups", Supplement D: Chapters 19 and 22, John Wiley & Sons Ltd. (1983), and Chapter 11, John Wiley & Sons Ltd. (1995).

The use of catalytic amounts of Lewis acids in the halogenation of activated methylene and methine compounds with electrophilic halogenation reagents has not yet been described. Nor has enantioselective halogenation of racemic methine compounds using catalytic amounts of optically active Lewis acids been disclosed either.

It has now been found, surprisingly, that catalytic amounts of certain titanium(IV) halides are able to speed up the halogenation of activated methylene and methine compounds with electrophilic halogenation reagents, and halogenation can be achieved with high yields in considerably shorter reaction times. In addition, the selectivity of mono-halogenation of activated methylene compounds is considerably improved. It has also been found for the first time, surprisingly, that enantioselective halogenation of activated racemic methine compounds can also be carried out catalytically if titanium(IV) dihalides to which a chiral alkane-1,3-, -1,4- or -1,5-diolate is covalently bonded are used as catalyst. The halogenation can in fact take place under mild reaction conditions such as, for example, room temperature.

One aspect of the invention is a process for the halogenation of activated methylene and methine compounds with at least equimolar amounts of an electrophilic halogenation reagent, which comprises reacting said activated methylene and methine compounds in the presence of catalytic amounts of a titanium compound of the formula I or of a titanium compound of the formula II

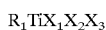

$$R_1TiX_1X_2X_3 \quad \text{(I)},$$

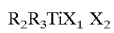

$$R_2R_3TiX_1X_2 \quad \text{(II)},$$

in which

R₁ is chlorine, bromine or iodine, a substituted or unsubstituted cyclopentadienyl or indenyl, and X₁, X₂ and X₃ are, independently of one another, chlorine, bromine or iodine, or X₁, X₂ and X₃ are an organic sulfonate group where R₁ is a substituted or unsubstituted cyclopentadienyl or indenyl;

R₂ and R₃ are a substituted or unsubstituted cyclopentadienyl or indenyl, R₂ and R₃ together are a substituted or unsubstituted and bridged or unbridged biscyclopentadienyl or bisindenyl, or R₂ and R₃ together are a substituted or unsubstituted 1,3-, 1,4- or 1,5-diolate, and X₁ and X₂ are, independently of one another, chlorine, bromine or iodine or an organic sulfonate group.

Activated methylene and methine compounds are to be understood as meaning for the purposes of the invention organic compounds to whose methylene or methine group at least two highly electron-attracting, or at least one highly electron-attracting and mesomerizing, or two electron-attracting and mesomerizing, groups are bonded. Examples of such groups are imine, keto, thioketo, aldehyde, carboxylate, carboxamide, nitrile, sulfoxide, sulfone, nitro, phosphonate, phosphine oxide and phosphonium groups. Preferred groups are imine, keto, carboxylate, carboxamide and nitrile groups. Highly electron-attracting groups are particularly preferably nitrile groups; the other aforementioned groups are electron-attracting and mesomerizing. Some examples of such groups of activated methylene and methine compounds are malonic diesters, malonamides, malononitrile, cyanoacetic esters and keto compounds; particular preference is given to β-diketones and β-keto carboxylic esters having 1 to 20 C atoms in the ester group. It has proved advantageous to employ for the halogenation those activated methylene and methine compounds which have a finite enol or enamine content and, among these, especially those able to form chelates with the titanium atom.

Examples of suitable activated methylene and methine compounds are saturated or unsaturated aliphatic, cycloaliphatic, heteroaliphatic and heterocycloaliphatic compounds having hetero atoms selected from the group of O, S and N and containing 2 to 30, preferably 2 to 20, and particularly preferably 2 to 16, C atoms. The cycloaliphatic and heterocycloaliphatic compounds may be mono- or polycyclic fused and/or bridged rings containing 3 to 16, preferably 3 to 12 and particularly preferably 4 to 8, ring members. Aromatic and/or heteroaromatic systems may also be fused to one or more rings. The compounds may be unsubstituted or substituted by —CN, —NH₂, C₁–C₁₈alkyl, C₁–C₁₈alkoxy, C₁–C₈haloalkyl, —NH(C₁–C₁₂alkyl), —(C₁–C₁₂alkyl)₂, —SO₃M, —COOM, —COOH, —COOC₁–C₂₀alkyl or -phenyl or -benzyl or -diphenylmethyl, —CO—NH₂, —CO—NH(C₁–C₁₂alkyl), —CO—N(C₁–C₁₂alkyl)₂, C₅–C₁₂cycloalkyl, C₅–C₁₂cycloalkoxy, C₅–C₁₂heterocycloalkyl or C₅–C₁₂heterocycloalkoxy having 1 to 3 hetero atoms selected from the group of O, S and N, C₆–C₁₂ aryl or C₆–C₁₂aryloxy, C₄–C₁₁heteroaryl or C₄–C₁₁heteroaryloxy having 1 to 3 hetero atoms selected from the group of O, S and N, C₇–C₁₂aralkyl or C₅–C₁₂heteroaralkyl having 1 to 3 hetero atoms selected from the group of O, S and N, where M is Li, Na or K. Cyclic substituents may be unsubstituted or substituted, for example by halogen (preferably F, Cl or Br), —CN, C₁–C₈alkyl, C₁–C₄haloalkyl, C₁–C₈alkoxy or other aforementioned substituents. The compounds may contain one or more substituents.

Such activated methylene and methine compounds may, for example, have the formulae III and IV,

$$NC—CH(R_4)—CN \quad (III),$$

$$R_5—CH(R_4)—C(=O)—R_6 \quad (IV),$$

in which R₄ is hydrogen, linear or branched C₁–C₁₈alkyl, C₂–C₁₈alkenyl, C₃–C₁₂cycloalkyl, C₃–C₁₂cycloalkenyl, C₃–C₁₂cycloalkyl-C₁–C₆alkyl, C₃–C₁₂cycloalkenyl-C₁–C₆alkyl, C₆–C₁₈aryl, C₇–C₁₈aralkyl, C₈–C₁₈aralkenyl, or C₃–C₁₂heterocycloalkyl, C₃–C₁₂heterocycloalkenyl, C₃–C₁₂ heterocycloalkyl-C₁–C₆alkyl, C₃–C₁₂heterocycloalkenyl-C₁–C₆alkyl, C₄–C₁₈heteroaryl, C₅–C₁₈heteroaralkyl, each of which is bonded via a C atom and has hetero atoms selected from the group of O, S and N;

R₅ is —CN or a —C(=O)—R₇ group;

R₆ independently has the same meanings as R₄ or is linear or branched C₁–C₁₈alkoxy, C₃–C₁₂cycloalkoxy C₃–C₁₂cycloalkyl-C₁–C₆alkoxy, C₆–C₁₈aryloxy, C₇–C₁₈aralkyloxy, C₃–C₁₂heterocycloalkyloxy, C₃–C₁₂heterocycloalkyl-C₁–C₆alkyloxy, C₄–C₁₈heteroaryloxy, C₅–C₁₈heteroaralkyl having hetero atoms selected from the group of O, S and N;

R₇ is linear or branched C₁–C₁₈alkyl, C₂–C₁₈alkenyl, C₃–C₁₂cycloalkyl, C₃–C₁₂cycloalkenyl, C₃–C₁₂cycloalkyl-C₁–C₆alkyl, C₃–C₁₂cycloalkenyl-C₁–C₆alkyl, C₆–C₁₈aryl, C₇–C₁₈aralkyl, or C₃–C₁₂heterocycloalkyl, C₃–C₁₂heterocycloalkenyl, C₃–C₁₂heterocycloalkyl-C₁–C₆alkyl, C₃–C₁₂heterocycloalkenyl-C₁–C₆alkyl, C₄–C₁₈heteroaryl, C₅–C₁₈heteroaralkyl, each of which is bonded via a C atom and has hetero atoms selected from the group of O, S and N, linear or branched C₁–C₁₈alkoxy, C₃–C₁₂cycloalkoxy, C₃–C₁₂cycloalkyl-C₁–C₆alkoxy, C₆–C₁₈aryloxy, C₇–C₁₈aralkyloxy, C₃–C₁₂heterocycloalkyloxy, C₃–C₁₂heterocycloalkyl-C₁–C₆alkyloxy, C₄–C₁₈heteroaryloxy, C₅–C₁₈heteroaralkyl having hetero atoms selected from the group of O, S and N;

R₄ and R₆ together with the group —C—C(=O)— to which they are bonded are an aliphatic or heteroaromatic, saturated or unsaturated, single or polycyclic ring which contains 3 to 18 ring members and to which aromatic or heteroaromatic rings may be fused;

R₆ and R₇ together with the group —(O=)C—C—C(=O)— to which they are bonded are an aliphatic or heteroaromatic, saturated or unsaturated, single or polycyclic ring which contains 3 to 18 ring members and to which aromatic or heteroaromatic rings may be fused; where R₄, R₅, R₆ and R₇ are unsubstituted or substituted as defined above for methylene and methine compounds.

If R₄, R₆ and R₇ are alkyl, it preferably contains 1 to 12 and particularly preferably 1 to 8 C atoms. If R₄, R₆ and R₇ are alkenyl, it preferably contains 2 to 12 and particularly preferably 2 to 8 C atoms. If R₄, R₆ and R₇ are cycloalkyl or cycloalkenyl, the latter are preferably C₃–C₈cycloalkyl and C₃–C₈cycloalkenyl respectively. If R₄, R₆ and R₇ are cycloalkylalkyl or cycloalkenylalkyl, the latter are preferably C₃–C₈cycloalkyl-C₁–C₄alkyl and C₃–C₈cycloalkenyl-C₁–C₄alkyl respectively. If R₄, R₆ and R₇ are C₆–C₁₈aryl, C₇–C₁₈aralkyl, the latter are preferably C₆–C₁₄aryl, particularly preferably C₆–C₁₀aryl, and C₆–C₁₄aryl-C₁–C₆alkyl, and particularly preferably C₆–C₁₀aryl-C₁–C₄alkyl, respectively. If R₄, R₆ and R₇ are heterocycloalkyl or heterocycloalkenyl, the latter are preferably C₄–C₈heterocycloalkyl and C₄–C₈ heterocycloalkenyl respectively. If $R_4$, $R_6$ and $R_7$ are heterocycloalkylalkyl or heterocycloalkenylalkyl, the latter are preferably $C_4$–$C_8$heterocycloalkyl-$C_1$–$C_4$alkyl and $C_4$–$C_8$heterocycloalkenyl-$C_1$–$C_4$alkyl respectively. If $R_4$, $R_6$ and $R_7$ are heteroaryl or heteroaralkyl, the latter are preferably $C_4$–$C_{14}$heteroaryl and particularly preferably $C_4$–$C_{10}$heteroaryl, and $C_4$–$C_{14}$heteroaryl-$C_1$–$C_6$alkyl and particularly preferably $C_4$–$C_{10}$heteroaryl-$C_1$–$C_4$alkyl, respectively. The same preference is applied to the oxy radicals. Heterocycles preferably contain 1 to 3 and particularly preferably one or two hetero atoms selected from the group of O, S and N.

If $R_4$ and $R_6$, or $R_6$ and $R_7$, together form a ring, this preferably contains 3 to 12 ring members. The ring may contain one or more hetero atoms, preferably 1 to 3 and particularly preferably 1 or 2 hetero atoms. It is very particularly preferred for $R_4$ and $R_6$ together and $R_6$ and $R_7$ to have the formula —$(CH_2)_m$—$(O)_n$— in which m is a number from 1 to 10 and n is 0 or 1.

Some examples of $R_4$, $R_6$ and $R_7$ are indicated below, which also apply analogously to oxy radicals.

Examples of alkyl and alkenyl are methyl, ethyl, n- and i-propyl, n-, i- and t-butyl, pentyl, i-pentyl, hexyl, heptyl, octyl, nonyl, decyl, undecyl, dodecyl, vinyl and allyl. A preferred group is methyl, ethyl, n- and i-propyl, n-, i- and t-butyl.

Examples of cycloalkyl and cycloalkenyl are cyclopropyl, cyclobutyl, cyclopentyl, cyclohexyl, cycloheptyl and cyclooctyl, and cyclopentenyl, cyclohexenyl and cyclohexadienyl. Particular preference is given to cyclobutyl, cyclopentyl, cyclohexyl, cyclohexenyl, cyclopentenyl and cyclohexadienyl.

Examples of cycloalkylalkyl and cycloalkenylalkyl are cyclopentylmethyl, cyclopentylethyl, cyclohexylmethyl, cyclohexylethyl and cyclohexenylmethyl.

Examples of aryl are naphthyl and, in particular, phenyl.

Examples of aralkyl and aralkenyl are benzyl, diphenylmethyl, naphthylmethyl, β-phenylethyl, β-phenylethenyl and phenylpropyl.

Examples of heterocycloalkyl and heterocycloalkenyl are pyrrolidinyl, pyrrolinyl, tetrahydrofuranyl, dihydrofuranyl and piperanzinyl.

Examples of heterocycloalkylalkyl and heterocycloalkenylalkyl are pyrrolidinylmethyl or ethyl, or -propyl, pyrrolinylmethyl or -ethyl or -propyl, tetrahydrofuranylmethyl or -ethyl or propyl, dihydrofuranylmethyl or -ethyl or -propyl and piperazinylmethyl or -ethyl or -propyl.

Examples of heteroaryl are pyridinyl, pyrimidinyl, pyrazinyl, pyrrolyl, furanyl, oxazolyl, imidazolyl, benzofuranyl, indolyl, benzimidazolyl, quinolinyl, isoquinolinyl, quinazolinyl, quinoxalinyl.

Examples of heteroaralkyl are pyridinylmethyl or -ethyl or -propyl, pyrimidinylmethyl or -ethyl or -propyl, pyrrolylmethyl or -ethyl or -propyl, furanylmethyl or -ethyl or -propyl, imidazolylmethyl or -ethyl or -propyl, indolylmethyl or -ethyl or -propyl.

Large numbers of electrophilic halogenation reagents are known. Among the fluorination reagents, those most frequently used are inert gas fluorides, fluoroalkoxyfluorides, sulfonyl fluorides, N-fluorinated pyridinium salts, tertiary N-fluoroammonium salts, N-fluorinated amides and imides, $FClO_3$ and $F_2$ itself. A review of fluorination reagents is to be found, for example, in Chem. Rev. 1996, 96,1717–1736 by S. Rozen and in Chem. Rev. 1996, 96, 1737 to 1755 by G. Sankar Lal et al. Some fluorination reagents can be purchased.

Among the inert gas fluorides, particular mention should be made of xenon difluoride. An example of fluoroalkoxylfluorides is $(CF_3)_2CFOF$. Of the sulfonyl fluorides, $CF_3SO_2F$ is frequently used. The N-fluorinated pyridinium salts are internal salts of pyridines and bipyridyls substituted by sulfo grups, or triflates or tetrafluoroborates. Among the amides, particular mention should be made of N-alkylated and N-fluorinated sulfonamides, carboxamides, lactams and sultams. N-fluorinated imides are, in particular, dicarboximides or disulfonimides.

Preference is given according to the invention to tertiary N-fluoroammonium salts, especially 1-substituted 4-fluoro-1,4-diazoniabicyclo[2,2,2]octane salts with complex anions, for example $BF_4$, $AsF_6$, $PF_6$ or $SbF_6$. Suitable substituents are $C_1$–$C_4$alkyl, $C_1$–$C_4$hydroxyalkyl and $C_1$–$C_4$haloalkyl. A specific example is 1-chloromethyl- or 1-hydroxymethyl-4-fluoro-1,4-diazoniabicyclo[2,2,2]octane bistetrafluoroborate (Selectfluor™), which is commercially available.

Large numbers of electrophilic chlorinating, brominating and iodinating agents are likewise known, and some of them are commercially available. Possibilities are $Cl_2$, $Br_2$ or $I_2$ or interhalogen compounds, for example BrCl or ICl, and in particular N-chlorinated, N-brominated and N-iodinated dicarboximides or disulfonimides, lactams and sultams. Examples of such imides are succinimide, phthalimide, naphthalene-1,2-, -2,3- or 1,8-dicarboximide and biphenyl-2,2'-dicarboximide. Further examples are monoalkyl dihalides, dialkyl monohalides and N-chlorinated, N-brominated and N-iodinated N-alkyl- or N-arylcarboxamides and -sulfonamides.

$X_1$, $X_2$ and $X_3$ in compounds of the formula I are preferably bromine and particularly preferably chlorine. Cyclopentadienyl and indenyl may, for example, be substituted by $C_1$–$C_4$alkyl, particularly methyl, $C_1$–$C_4$alkoxy, chlorine or bromine, trimethylsilyl, phenyl, benzyl, cyclohexyl, trimethylene and tetramethylene. Preferred examples are cyclopentadienyl, methylcyclopentadienyl, dimethylcyclopentadienyl, trimethylcyclopentadienyl, tetramethylcyclopentadienyl, pentamethylcyclopentadienyl and trimethylsilylcyclopentadienyl.

Examples of sulfonate groups are aromatic sulfonates such as phenylsulfonate, tosylate and, in particular, trifluoromethylsulfonate (triflate). Preferred titanium compounds of the formula I are titanium tetrachloride, titanium tetrabromide, cyclopentadienyltitanium trichloride and cyclopentadienyltitanium tribromide.

If $R_2$ and $R_3$ in formula II together are a bridged cyclopentadienyl or indenyl, the bridging group may be, for example, —Si(CH$_3$)$_2$- or $C_1$–$C_4$alkylene, preferably ethylene. Suitable substituents have been mentioned above for cyclopentadienyl. If $X_1$ and $X_2$ are halogen, they are preferably Br and, in particular, Cl. $R_2$ and $R_3$ are preferably a 1,3-, 1,4- or 1,5-diolate.

Diolates are understood as meaning for the purposes of the invention divalent radicals of diols whose hydroxyl groups are bonded in the 1,3, 1,4 or 1,5 positions of a substituted or unsubstituted $C_3$, $C_4$ or $C_5$ chain in an open-chain, cyclic or cyclic-aliphatic compound. Corresponding 1,4-diolates are preferred, these also encompassing 1,1'-bicyclic hydrocarbons with hydroxyl groups bonded in the 2,2' position. Large numbers of 1,3-, 1,4-or 1,5-diols for preparing the titanium diolate dihalides used as catalyst are known, and some of them can be purchased.

If $R_2$ and $R_3$ together are a substituted or unsubstituted 1,3-, 1,4- or 1,5-diolate, they are propane-1,3-, butane-1,4- and pentane-1,5-diolates, which are unsubstituted or substituted, for example by 1 to 6 or 1 to 3 substituents, or in which a $C_2$ or $C_3$ unit of the C chains form together with two substituents a 4- to 8-membered, preferably 5- to 7-membered, mono-, bi- or tricyclic hydrocarbon ring which is unsubstituted or substituted. Suitable 1,4-diolates may also be derived from unsubstituted or substituted bicyclic 2,2'-diols, for example biphenyl-2,2'-dioxy, dinaphthyl-2,2'-dioxy, bicyclohexyl-2,2'-dioxy and bicyclopentyl-2,2'-dioxy.

Examples of suitable substituents are halogen, $C_1$–$C_8$alkyl and preferably $C_1$–$C_4$alkyl, $C_3$–$C_8$cycloalkyl and preferably $C_5$–$C_6$cycloalkyl, $C_3$–$C_8$cycloalkyl-$C_1$–$C_4$alkyl and preferably $C_5$–$C_6$cycloalkylmethyl or -ethyl, $C_6$–$C_{10}$aryl and preferably phenyl or naphthyl, $C_7$–$C_{12}$aralkyl and preferably benzyl and phenylethyl, and, bonded in the 2 or 3 position, $C_1$–$C_8$alkoxy and preferably $C_1$–$C_4$alkoxy, $C_3$–$C_8$cycloalkoxy and preferably $C_5$–$C_6$cycloalkoxy, $C_3$–$C_8$cycloalkyl-$C_1$–$C_4$alkoxy and preferably $C_5$–$C_6$cycloalkylmethoxy or -ethoxy, $C_6$–$C_{10}$aryloxy and preferably phenyloxy or naphthyloxy, $C_7$–$C_{12}$aralkyloxy and preferably benzyloxy and phenylethoxy, or, bonded in the 2,3 position and unsubstituted or substituted by a hydrocarbon radical as defined above, trimethylene, tetramethylene, ethylene-1,2-dioxy or methylenedioxy. Cyclic substituents may in turn be substituted, for example, by $C_1$–$C_4$alkyl, $C_1$–$C_4$alkoxy or halogen.

On use of activated racemic methine compounds in the process of the invention, optical inductions and enantioselective halogenations are surprisingly achieved when the titanium catalyst comprises an optically active diolate, in particular an optically active propane-1,3-, butane-1,4- or pentane-1,5-diolate as ligand. This is the first catalysed process for enantioselective halogenation. Optical yields of up to 85% ee and more can be achieved.

In a preferred embodiment, the process of the invention for enantioselective halogenation is carried out in the presence of catalytic amounts of titanium compounds of the formula II in which $R_2$ and $R_3$ together are an enantiopure substituted propane-1,3-, butane-1,4- or pentane-1,5-dioxy. Preferred titanium compounds of the formula II are those in which $R_2$ and $R_3$ together are enantiopure substituted butane-1,4-dioxy radicals, which induce particularly high optical yields as catalysts in the halogenation.

The butane-1,4-dioxy may, for example, have the formula V or VI

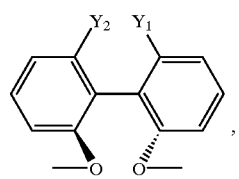

(V)

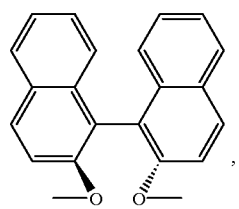

(VI)

in which $Y_1$ and $Y_2$ are a substituent, for example $C_1$–$C_4$alkyl, $C_1$–$C_4$alkoxy or halogen, and 5- or 6-membered carbocyclic rings can be fused to the benzene rings.

Butane-1,4-diolates which are more preferably used contain at least one stereogenic C atom. The stereogenic C atoms are preferably located in the 2 or in the 2 and 3 positions of the butane chain. The stereogenic C atoms may, however, also be located in the 1 or in the 1 and 4 positions of the butane chain. The C atoms in the 1 and 4 positions may be substituted by hydrocarbon radicals which preferably contain 1 to 12 and particularly preferably 1 to 8 C atoms. The C atoms in the 2 and 3 positions may be substituted by hydrocarbon radicals and/or by hydrocarbon oxy radicals which preferably contain 1 to 12 and particularly preferably 1 to 8 C atoms, it being possible for two substituents in the 2 and 3 positions to form together with the C atoms to which they are bonded a 3- to 8- and preferably a 5- or 6-membered carbocyclic ring, or a dioxolane ring.

The butane-1,4-diolates particularly preferably have the formula VII

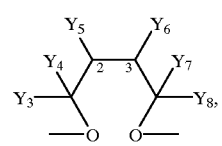

(VII)

in which $Y_3$, $Y_4$, $Y_5$, $Y_6$, $Y_7$ and $Y_8$ are, independently of one another, a hydrogen atom, $C_1$–$C_8$alkyl and preferably $C_1$–$C_4$alkyl, $C_3$–$C_8$cycloalkyl and preferably $C_5$–$C_6$cycloalkyl, $C_3$–$C_8$cycloalkyl-$C_1$–$C_4$alkyl and preferably $C_5$–$C_6$cycloalkylmethyl or -ethyl, $C_6$–$C_{10}$aryl and preferably phenyl or naphthyl, $C_7$–$C_{12}$aralkyl and preferably benzyl and phenylethyl;

$Y_5$ and $Y_6$ are $C_1$–$C_8$alkoxy and preferably $C_1$–$C_4$alkoxy, $C_3$–$C_8$cycloalkoxy and preferably $C_5$–$C_6$cycloalkoxy, $C_3$–$C_8$cycloalkyl-$C_1$–$C_4$alkoxy and preferably $C_5$–$C_6$cycloalkylmethoxy or ethoxy, $C_6$–$C_{10}$aryloxy and preferably phenyloxy or naphthyloxy, $C_7$–$C_{12}$aralkyloxy and preferably benzyloxy and phenylethyloxy;

$Y_5$ and $Y_6$ are, together with the C atoms to which they are bonded, $C_5$–$C_8$cycloalkyl; or $Y_5$ and $Y_6$ are, together with the C atoms to which they are bonded, the radical —O—$CY_9Y_{10}$—O—;

$Y_9$ and $Y_{10}$ are, independently of one another, a hydrogen atom, $C_1$–$C_8$alkyl and preferably $C_1$–$C_4$alkyl, $C_3$–$C_8$cycloalkyl and preferably $C_5$–$C_6$cycloalkyl, $C_3$–$C_8$cycloalkyl-$C_1$–$C_4$alkyl and preferably $C_5$–$C_6$cycloalkylmethyl or -ethyl, $C_6$–$C_{10}$aryl and preferably phenyl or naphthyl, $C_7$–$C_{12}$aralkyl and preferably benzyl and phenylethyl;

$Y_3$, $Y_4$, $Y_5$, $Y_6$, $Y_7$, $Y_8$, $Y_9$ and $Y_{10}$ are unsubstituted or substituted by halogen, $C_1$–$C_4$alkyl or $C_1$–$C_4$alkoxy;

with the proviso that at least one of $Y_3$, $Y_4$, $Y_5$, $Y_6$, $Y_7$, $Y_8$, $Y_9$ and $Y_{10}$ is one of said radicals.

The preferences and exemplary embodiments indicated above apply to the radicals.

$Y_5$ and $Y_6$ in formula VII are, together with the C atoms to which they are bonded, preferably $C_5$–$C_8$cycloalkyl or the radical —O—$CY_9Y_{10}$—O—.

Particularly preferred compounds of the formula VII are (4R,5R)- and (4S,5S)-4,5-bis(diphenylhydroxymethyl)-2,2-dimethyldioxolane, and (4R,5R)- and (4S,5S)-4,5-bis(di-1-naphthylhydroxymethyl)-2,2-dimethyldioxolane, which are commercially available.

Further examples of enantiopure diolates are those of the formulae

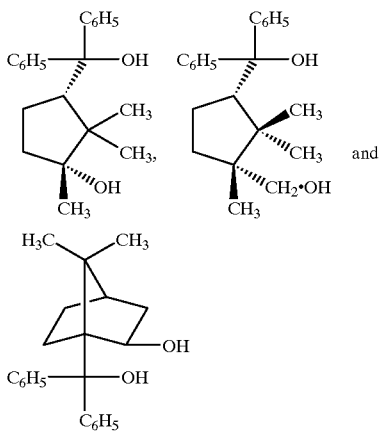

The catalysts to be used according to the invention are known or can be obtained by methods known from the literature (for example Beck et al., Chimia 1991, 45, page 238 and D. Seebach et al., J. Org. Chem. 1995, 60, pages 1788 to 1799, and D. Seebach et al., Helvetica Chimica Acta, 82, (1999), pages 1829 to 1842) by, for example, reacting titanium dihalide diisopropoxide with diols. The catalysts can be prepared in situ and be used in the process of the invention, or the catalysts can be isolated and employed as such. Isolated catalysts may be in the form of solvates of solvents used for their preparation.

A catalytic amount may mean for the purposes of the invention 0.5 to 20 mol %, preferably 1 to 15 mol %, and particularly preferably 2 to 10 mol %, based on the activated methylene or methine compounds.

The halogenation reagents are generally used in equimolar amounts or a slight excess based on the activated methylene or methine compounds. It may be advantageous to add the fluorination reagent in portions or continuously during the reaction, especially in the monofluorination of activated methylene compounds.

The process can be carried out at temperatures from −40° C. to 120° C., preferably 20° C. to 100° C., and particularly preferably 0 to 80° C. Lower temperatures are beneficial for the enantiomeric excess.

The process of the invention may be carried out with or without solvent. Examples of suitable solvents are aliphatic, cycloaliphatic and aromatic hydrocarbons (pentane, hexane, petroleum ether, cyclohexane, methylcyclohexane, benzene, toluene, xylene), halogenated aliphatic hydrocarbons (methylene chloride, chloroform, di- and tetrachloroethane), nitriles (acetonitrile, propionitrile, benzonitrile), ethers (diethyl ether, dibutyl ether, t-butyl methyl ether, ethylene glycol dimethyl ether, ethylene glycol diethyl ether, diethylene glycol dimethyl ether, tetrahydrofuran or dioxane), ketones (acetone, methyl isobutyl ketone), carboxylic esters and lactones (ethyl and methyl acetates, valerolactone), N-substituted lactams (N-methylpyrrolidone), carboxamides (dimethylacetamide, dimethylformamide), acyclic ureas (tetramethylurea) or cyclic ureas (dimethylimidazolidinone), and sulfoxides and sulfones (dimethyl sulfoxide, dimethyl sulfone, tetramethylene sulfoxide, tetramethylene sulfone), alcohols (methanol, ethanol, propanol, butanol, ethylene glycol monomethyl ether, ethylene glycol monoethyl ether, diethylene glycol monomethyl ether) and nitrohydrocarbons (nitromethane). The solvents can be employed alone or in any suitable mixtures.

The process is preferably carried without solvent or in solvents such as N,N-dialkylated carboxamides and lactams, for example dimethylacetamide, dimethylformamide, N-methylpyrrolidone, and propylene carbonate, dimethyl sulfoxide, dioxane, acetonitrile, nitromethane or alcohols.

The process of the invention is preferably carried out with exclusion of water. It is expedient to dry the chemicals used, such as solvents, beforehand, or to add water-binding agents such as molecular sieves.

The isolation and purification of the halogenated compounds can take place by methods known per se, for example distillation, crystallization, recrystallization and chromatographic methods.

The halogenated compounds obtainable according to the invention are valuable intermediates for preparing pesticides and active pharmaceutical ingredients. Thus, W. J. Middleton describes, in J. of Fluorine Chemistry 100 (1999), pages 207–216, the efficacy of 3-fluorodiazepam, a derivative of Valium®. R. Filler et al. describe, in Biomedicinal Aspects of Fluorine Chemistry, Elsevier Biomedical Press (Amsterdam-New York-Oxford 1982), the efficacy of fluorinated active ingredients, for example 4-fluorofarnesol, as insect attracter. Chlorinated, brominated and iodinated compounds are valuable intermediates which can easily be derivatized, for example to give OH, $NH_2$, alkoxy or alkyl derivatives. In the case of enantiopure intermediates this makes it possible to prepare the required stereoisomer specifically with inversion at the stereogenic C atom.

The following examples illustrate the invention in more detail. The following abbreviations are used:
TLC: thin-layer chromatography, FC: flash chromatography, MeCN: acetonitrile; DME: 1,2-dimethoxyethane, MS: molecular sieves, RT: room temperature, RE: rotary evaporator, HV: high vacuum, TBME: tert-butyl methyl ether.
F-TEDA: 1-chloromethyl-4-fluoro- 1 ,4-diazoniabicyclo[2, 2,2]octane bistetrafluoroborate (Selectfluor®)
NFSI: N-fluorodibenzenesulfonimide,
NCS: N-chlorosuccinimide
R-TADDOL: (4R,5R)-4,5-bis(diphenylhydroxymethyl)-2, 2-dimethyldioxolane
α-Naphthyl-TADDOL: (4R-trans)-2,2,-dimethyl-α,α,α',α'-tetra(1-naphthyl)-1,3-dioxolane-4,5-dimethanol
β-Naphthyl-TADDOL: (−)-2,3-O-isopropylidene-1,1,4,4-tetra(2-naphthyl)-L-threitol
R-Binol: R(+)-1,1'-bi(2-naphthol)
A) Preparation of Catalysts

EXAMPLE A1

Catalyst C1

1.119 g of R-TADDOL (2.4 mmol) are added to a solution of 565 mg of $TiCl_2$(i-propoxide)$_2$ (2.38 mmol) in 20 ml of toluene and stirred for 20 minutes. The solvent is then removed under HV, and the residue is dried under high vacuum. The foam-like residue (1.506 g, 78%) is ground to a powder which can be weighed for the catalysis experiments. According to $^1$H-NMR, the reaction product also contains free TADDOL, isopropanol and toluene.

EXAMPLE A2

Catalyst C2

Under argon, 1.25 ml of a solution of $TiCl_2$(i-propoxide)$_2$ in MeCN (1.0 M, 1.25 mmol) are added dropwise to a suspension of 606 mg of R-TADDOL (1.30 mmol) in 10 ml of MeCN in a Schienk flask. The solution is stirred at RT for 20 hours and then evaporated to dryness under HV. The solid is dried under high vacuum for one day and then dissolved in 10 ml of MeCN (0.125 M). 0.1 ml of this solution is equivalent to 5 mol % catalyst for 0.25 mmol of substrate.

EXAMPLE A3

Catalyst C3

0.31 ml of a 1M solution of $TiCl_2$(i-propoxide)$_2$ in MeCN (0.31 mmol) is added dropwise to a solution of 217 mg of α-naphthyl-TADDOL (0.325 mmol) in 5 ml of MeCN, stirred at RT for 18 hours and then concentrated under high vacuum, whereupon a yellow powder crystallizes out. It is filtered off and dried under high vacuum for one day. The solid powder is mixed with 5 ml of MeCN and 4.0 ml of tetrahydrofuran. This results in a clear yellow solution (0.033 M). 0.38 ml is equivalent to 0.0125 mmol, or 5 mol % for 0.25 mmol of substrate.

EXAMPLE A4

Catalyst C4

The process is carried out in analogy to Example A3 with 170 mg of β-naphthyl-TADDOL (0.255 mmol), 5 ml of MeCn and 0.25 ml of 1 M solution of $TiCl_2$(i-propoxide)$_2$ in MeCN (0.25 mmol). A pale yellow foam is obtained and is dissolved in 5 ml of MeCN. 0.25 ml is equivalent to 0.0125 mmoll, or 5 mmol % for 0.25 mmol of substrate.

EXAMPLE A5

Catalyst C5

About 60 mg of 3 Å molecular sieve are added to 287 mg (1 mmol) of R-binol in 9 ml of MeCN and, while stirring, 0.98 ml of a 1 M solution of $TiCl_2$(i-propoxide)$_2$ in MeCN is added dropwise. A deep brownish red solution (0.1 M) is obtained. 0.15 ml is equivalent to 0.0125 mmol, or 5 mol % for 0.25 mmol of substrate.

slowly concentrated under HV to a volume of about 8 ml, resulting in a gelatinous mass which is eventually all converted into white crystals. These are dissolved in 20 ml of MeCN and, after addition of 0.65 ml of DME (6.25 mmol), the mixture is stirred briefly until homogeneous and left to stand at RT. White crystalline needles start to separate out after 20 seconds. After standing at RT for 1 hour and at −20° C. for 1 day, the mixture is filtered at −20° C. The remaining white crystals are washed at −20° C. (ice/NaCl) with 20 ml of MeCN, and the mother liquor is filtered off. Pure white crystals remain and, after drying under HV (0.002 mbar) for 1 day, have the composition [(R-TADDOLate)$TiCl_2$(DME)]+0.86 MeCN ($^1$H-NMR and elemental analysis). Yield 3.507 g (89%).

EXAMPLE A7

Catalyst C7

0.49 ml of $TiCl_2$(isopropoxide)$_2$ (1 M in MeCN, 0.49 mmol) is added dropwise to a solution of 340 mg of α-naphthyl-TADDOL (0.51 mmol) in 10 ml of MeCN at RT, whereupon the solution becomes yellow in colour. It is then stirred at RT for one day. The solution (about 0.047 M) is employed directly as catalyst.

B) Halogenations

The optical yield (ee) is determined on the isolated reaction product after dissolving in the mobile phase by HPLC on chiral columns. For this, 2.5 mg of product are dissolved in 0.8 ml of hexane, and 2 μl of this are used for the analysis.

Preparation of the F-TEDA Solution:

6 g of F-TEDA and 10 g of 3 Å MS are added to 100 ml of MeCN and stirred at RT overnight. The suspension is left to settle and the supernatant clear solution is used. Iodometric titration shows a content of 0.15 mol/100 ml.

The following substrates are employed in the fluorination:

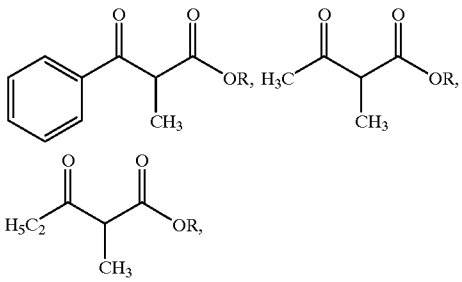

| | | |
|---|---|---|
| R = $C_2H_5$ | 1  R = $C_6H_5CH_2$ | 4  R = $(C_6H_5)_2CH$    7 |
| R = $C(CH_3)_2C_2H_5$ | 2  R = 1-naphthylmethyl | 5  R = 2,4,6-tri-i-propyl$C_6H_2CH_2$    8 |
| R = $(C_6H_5)_2CH$ | 3  R = 9-anthryl-$CH_2$ | 6 |

EXAMPLE A6

Catalyst C6

Under argon, 5.55 ml of $TiCl_2$(isopropoxide)$_2$ (1 M in MeCN; 5.55 mmol) are added dropwise to a suspension of 2.59 g of R-TADDOL (5.55 mmol) in 10 ml of MeCN and stirred at RT for one day, during which some white solid crystallizes and is redissolved by heating. The solution is concentrated under high vacuum (HV) and the solid residue is dried under HV at 40° C. for 8 hours. The residue is dissolved in 40 ml of MeCN at 50° C., and the solution is

EXAMPLES B1–B25

Fluorinations

Under argon, 1.0 ml of a 0.25 M solution of the substrate in MeCN and the catalyst are put in an oven-dried Schlenk flask with magnetic stirrer. After stirring for 15 minutes, 0.30 mmol of F-TEDA solution is added with a syringe at RT. After the reaction, the reaction mixture is washed with 35 ml of TBME and distilled water into a separating funnel, and the organic phase is separated off and filtered through a little alumina. The solvent is removed in an RE and the residue is dried at 45° C. in vacuo for 5 to 10 minutes. Unless indicated in Table 1, the yields are 50–99% of theory.

In Examples B1 and B13–B25, 100 mg of 3 Å MS are added.

In Examples B5 and B14, 2.8 equivalents of $NH_4ClO_4$ are added.

In Example B4, 20 mol % of tetraethylammonium chloride are added.

In Example B7, NFSI is used in place of F-TEDA.

The reaction temperatures are RT (B1, B4, B5, B9–B11, B13-B25), 0° C. (B2, B3, B12), 40° C. (B6 and B7) and 60° C. (B8).

The results are indicated in Table 1.

TABLE 1

| Example | Substrate | Catalyst (mol %) | Reaction time (h) | Yield (%) | ee (%) |
|---|---|---|---|---|---|
| B1 | 1 | C1 (5) | 10 | | 28 |
| B2 | 1 | C1 (5) | 10 | | 32 |
| B3 | 1 | C1 (10) | 10 | | 36 |
| B4 | 1 | C1 (5) | 30 | | 32 |
| B5 | 1 | C1 (5) | 30 | | 26.5 |
| B6 | 1 | C1 (5) | 10 | | 23 |
| B7 | 1 | C1 (5) | 50 | | 24 |
| B8 | 1 | C1 (5) | 2 | | 18 |
| B9 | 1 | C2 (10) | 10.5 | | 26 |
| B10 | 1 | C3 (5) | 40 | | 51 |
| B11 | 1 | C4 (5) | 12 | | 26 |
| B12 | 1 | C5 (5) | 10 | | −2^A) |
| B13 | 2 | C1 (5) | 2.5 | 62 | 29 |
| B14 | 2 | C1 (5) | 2.75 | 69 | 29 |
| B15 | 2 | C4 (5) | 2 | 75 | 33 |
| B16 | 3 | C7 (5) | 24 | | 69 |
| B17 | 4 | C6 (5) | 0.5 | | 37 |
| B18 | 4 | C7 (5) | 0.5 | | 55 |
| B19 | 5 | C2 (10) | 2.5 | 79 | 49 |
| B20 | 5 | C7 (5) | 0.5 | | 60 |
| B21 | 6 | C7 (5) | 0.5 | | 68 |
| B22 | 7 | C6 (5) | 2 | | 58 |
| B23 | 7 | C7 (5) | 1 | | 79 |
| B24 | 8 | C6 (5) | 0.5 | | 53 |
| B25 | 8 | C7 (5) | 0.5 | | 85 |

EXAMPLE B26

Fluorination of 2,4,6-triisopropylbenzyl 2-methyl-3-oxopentanoate

At 0° C., 444 mg of 2,4,6-triisopropylbenzyl 2-methyl-3-oxopentanoate (1.28 mmol) are dissolved in 10 ml of F-TEDA (0.145 M in MeCN, 1.45 mmol). After equilibration for 10 minutes, 1.28 ml of catalyst C7 (0.05 M in MeCN, 0.064 mmol, 5 mol %) are added dropwise and the resulting cloudy, lemon-yellow solution is stirred at 0° C. for 25 h. The reaction mixture is taken up in water and TBME, and the organic phase is separated off, washed twice with saturated aqueous NaCl solution and concentrated in an RE. Purification of the crude product by liquid chromatography (TBME/hexane 1:25) affords 416 mg (89%) of 2,4,6-triisopropylbenzyl 2-fluoro-2-methyl-3-oxopentanoate as colourless oil with an ee of 85.6%.

$^1$H-NMR (300 MHz, $CDCl_3$): 1.03 (t, J=7.2, 3H, $MeCH_2$), 1.22 (d, J=6.9, 6H, $Me_2CH$), 1.23 (d, J=6.9, 6H, $Me_2CH$), 1.26 (d, J=6.9, 6H, $Me_2CH$), 1.67 (d, $J_{FH}$=22.2, 3H, MECF), 2.61 (ddq, J=19.1, 7.1, 2.6, 1H, $MeCH_2$), 2.72 (ddq, J=19.2, 7.1, 3.5, 1H, $MeCH_2$), 2.89 (sept, J=7.0, 1H, $Me_2CH$), 3.13 (sept, J=6.9, 2H, $Me_2CH$), 5.33 (s, 2H, $OCH_2Ar$), 7.04 (s, 2H—Ar).

$^{13}$C-NMR (75.5 MHz, $CDCl_3$): 6.9 (d, $J_{FC}$=2), 20.1 (d, $J_{FC}$=23), 23.9, 24.3, 29.5, 30.5, 34.3, 61.4, 97.8 (d, $J_{FC}$=194), 121.2, 125.1, 149.0, 150.1, 167.2 (d, $J_{FC}$=25), 204.9 (d, $J_{FC}$=27).

$^{19}$F-NMR (188.3 MHz, $CDCl_3$): −159.1 (qt, $J_{FH}$=22.3, 2.9)

MS (EI): 365 (M$^+$, 0.3, 350 [M−Me]$^+$, 0.5), 321 (2), 258 (4), 217 ($[_iPr_3C_6H_2CH_2]^+$, 100), 202 (91),174 (17)

$[\alpha]_D$=+24.1 (c=1.11, methanol; sample with 85.6% ee)

EXAMPLE B27

Fluorination with $TiCl_4$ as Catalyst

At RT, 0.50 ml of a $TiCl_4$ solution in MeCN (0.13 M, 0.065 mmol, 6.5 mol %) is added dropwise to 206 mg of benzyl 2-methyl-3-oxobutanoate (1 mmol) and 380 mg of finely powdered F-TEDA (1.07 mmol) in 5 ml of MeCN, whereupon a pale reddish brown colour develops. After stirring at RT for 4 h, the now virtually colourless suspension is taken up in water and TBME, and the organic phase is separated off, washed three times with water, dried over $MgSO_4$ and concentrated to give 228 mg of pale yellow oil. The crude product is filtered with 5 ml of TBME/pentane (1:1) through a little alumina and, after concentration, affords 198 mg (96%) of benzyl 2-fluoro-2-methyl-3-oxobutanoate as colourless oil.

$^1$H-NMR (300 MHz, $CDCl_3$): 1.69 (d, $J_{FH}$=22.1, 3H, Me—CF), 2.28 (d, $J_{FH}$=4.6, 3H, Me—CO), 5.24 (s, 2H, $PhCH_2$), 7.30–7.41 (m, 5 H—Ph).

$^{13}$C-NMR (75.5 MHz, $CDCl_3$): 19.7 (d, $J_{FC}$=23), 24.9, 68.0, 97.6 (d, $J_{FC}$=194), 128.1, 128.6, 128.7, 134.6, 126.7 (d, $J_{FC}$=26), 202.1 (d, $J_{FC}$=29).

$^{19}$F-NMR (282 MHz, ($DCL_3$): −157.5 (qqq, $J_{FH}$=22.1, 4.5, 0.4).

MS (EI): 224 ([M$^+$]), 0.1), 196 (6), 162 (5), 136 (8), 91 (100).

EXAMPLE B28

9.0 mg of catalyst C6 (0.0127 mmol, 5 mol %) and 100 mg of powdered 3Å MS are added to 1.0 ml of a 0.25 M solution of benzyl 2-methyl-3-oxobutanoate in MeCN (0.25 mmol). At 0° C., 20 ml of F-TEDA (0.145 M in MeCN, 0.29 mmol) are added dropwise to the stirred suspension over the course of 5 minutes. After 3 h, the reaction mixture is taken up in TBME/water, and the organic phase is separated off, washed with water and filtered through a little alumina and cotton wool. Removal of the solvents leaves 54 mg of a colourless oil which consists of fluorination product and free ligand (R,R-TADDOL) and which is analysed by HPLC without further purification: HPLC (OJ, hexane/isopropanol 96:4, 1 ml/min; 210 nm): 16.30 min (smaller), 19.42 min (larger). The enantiomeric excess is 38.4% [(+)-product].

EXAMPLE B29

Monofluorination with Cyclopentadienyl $TiCl_3$ as Catalyst ($CpTiCl_3$)

At RT, 1.8 ml of F-TEDA in MeCN (0.26 mmol) are added to 67 mg of diphenylmethyl 3-oxobutanoate (0.25 mmol) and 2.9 mg of $CpTiCl_3$ (0.013 mmol, 5.3 mol %) and stirred for 5.5 h. Working up with TBME/water, washing the separated organic phase with water and filtration through alumina result in 73 mg of crude product which consists, according to $^1$H-NMR, of monofluorinated and difluorinated product in the ratio 11:1, with 91% conversion.

$^1$H-NMR (300 MHz, $CDCl_3$): monofluorinated product: 2.28 (d, $J_{FH}$=4.2, 3H, MeCO), 5.28 (d, $J_{FH}$=49.6, 1H, CHF), 6.98 (s, 1H, $CHPh_2$), 7.27–7.42 (m, 10 H—Ar); difluorinated product: 2.37 (t, $J_{FH}$=1.7, 3H, MeCO), 6.99 (s, 1H, $CHPh_2$), 7.27–7.42 (m, 10 H—Ar).

$^{19}$F-NMR (188.3 MHz, $CDCl_3$): monofluorinated product: −193.1 (dq, $J_{FH}$=49.5, 4.2); difluorinated product: −113.9 (q, $J_{FH}$=1.6).

EXAMPLE B30

Chlorination of Benzyl 2-methyl-3-oxobutanoate 100 mg of 3 Å MS and 35.5 mg of catalyst C6 (0.050 mmol, 5 mol %) are added to a solution of 206 mg of benzyl 2-methyl-3-oxobutanoate (1 mmol) in 4 ml of MeCN and stirred at 0° C. for 10 minutes. 154 mg of N-chlorosuccinimide (1.15 mmol) are added, and the mixture is stirred at 0° C. for 1.5 hours. The reaction mixture is extracted with TBME/water, and the organic phase is separated off, filtered through alumina, concentrated and fractionated by liquid chromatography (TBME/hexane 1:15). This results in 204 mg (85%) of benzyl 2-chloro-2-methyl-3-oxobutanoate as colourless liquid.

HPLC analysis reveals an ee of 48.0%.

$^1$H-NMR (300 MHz, CDCl$_3$): 1.84 (s, 3H, MeCCl), 2.30 (s, 3H, MeCO), 5.23 (d, J=17.1, 1H, CH$_2$Ph), 5.26 (d, J=17.1, 1H, CH$_2$Ph), 7.30–7.42 (m, 5 H—Ph).

$^{13}$C-NMR (62.9 MHz, CDCl$_3$): 24.1, 25.1, 68.4, 70.6, 128.1, 128.6, 128.6, 134.5, 167.7, 198.5.

MS (EI): 241 (M$^+$, 7), 205 ([M—Cl]+, 79), 198 ([M—Ac]+, 53), 181 (16), 162 (65), 91 (100)

HPLC (OJ, hexane/isopropanol 99:1, 0.7 ml/min): 25.1 min (smaller), 29.3 min (larger). [α]$_D$: −4.0 (c=1.215, methanol; sample with 48.0% ee).

What is claimed is:

1. A process for halogenation of an activated methylene or methine compound with at least equimolar amounts of an electrophilic halogenation reagent, which comprises reacting said activated methylene or methine compound with said electrophilic halogenation reagent in the presence of a catalytic amount of a titanium compound of the formula I or of a titanium compound of the formula II

$R_1TiX_1X_2X_3$            (I),

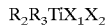

$R_2R_3TiX_1X_2$            (II), in which

R$_1$ is chlorine, bromine or iodine, a substituted or unsubstituted cyclopentadienyl or indenyl, and X$_1$, X$_2$ and X$_3$ are, independently of one another, chlorine, bromine or iodine, or X$_1$, X$_2$ and X$_3$ are an organic sulfonate group where R$_1$ is a substituted or unsubstituted cyclopemtadienyl or indenyl; R$_2$ and R$_3$ are a substituted or unsubtitued cyclopentadienyl or indenyl, R$_2$ and R$_3$ together are a substituted or unsubstituted and bridged or unbridged biscyclopentadienyl or bisindenyl, or R$_2$ and R$_3$ together are a substituted or unsubstituted 1,3-, 1,4- or 1,5-diolate, and X$_1$ and X$_2$ are, independently of one another, chlorine, bromine or iodine or an organic sulfonate group.

2. The process according to claim 1, wherein the activated methylene or methine compound is a saturated or unsaturated aliphatic, cycloaliphatic, heteroaliphatic or heterocycloaliphatic compound having a hetero atom selected from the group of O, S and N and containing 2 to 30 C atoms, no system or aromatic or heteroaromatic system or both aromatic and heteroaromatic systems being fused to the ring of the cyclic compound, and the compound being unsubstituted or substituted by —CN, —NH$_2$, C$_1$–C$_{18}$alkyl, C$_1$–C$_{18}$alkoxy, C$_1$–C$_8$haloalkyl, —NH(C$_1$–C$_{12}$alkyl), —(C$_1$–C$_{12}$alkyl)$_2$, —SO$_3$M, —COOM, —COOH, —COOC$_1$–C$_{20}$alkyl or -phenyl or benzyl or -diphenylmenthyl, CO—NH$_2$, —CO—NH(C$_1$–C$_{12}$alkyl), —CO—N(C$_1$–C$_{12}$alkyl)$_2$, C$_5$–C$_{12}$cycloalkyl, C$_5$–C$_{12}$cycloalkoxy, C$_5$–C$_{12}$heterocycloalkyl or C$_5$–C$_{12}$heterocycloalkoxy having 1 to 3 hetero atoms selected from the group of O, S and N, C$_6$–C$_{12}$aryl or C$_6$–C$_{12}$aryloxy, C$_4$–C$_{11}$heteroaryl or C$_4$–C$_{11}$heteroaryloxy having 1 to 3 hetero atoms selected from the group of O, S and N, C$_7$–C$_{12}$aralkyl or C$_5$–C$_{12}$heteroalkyl having 1 to 3 hetero atoms selected from the group of O, S and N, where M is Li, Na or K, and cyclic substituents in turn being unsubstituted or substituted by halogen, —CN, C$_1$–C$_8$alkyl, C$_1$–C$_4$haloalkyl, C$_1$–C$_8$alkoxy or other aforementioned substituents.

3. The process according to claim 2, wherein the activated methylene and methine compounds are those of the formulae III and IV,

NC—CH(R$_4$)—CN            (III),

R$_5$—CH(R$_4$)—C(=O) . R$_6$            (IV), in which R$_4$ is hydrogen, linear or branched C$_1$–C$_{18}$alkyl, C$_2$–C$_{18}$alkenyl, C$_3$–C$_{12}$cycloalkyl, C$_3$–C$_{12}$cycloalkenyl, C$_3$–C$_{12}$cycloalkyl-C$_1$–C$_6$alkyl, C$_3$–C$_{12}$cycloalkenyl-C$_1$–C$_6$alkyl, C$_6$–C$_{18}$aryl, C$_7$–C$_{18}$aralkyl, C$_8$–C$_{18}$aralkenyl, or C$_3$–C$_{12}$heterocycloalkyl, C$_3$–C$_{12}$heterocycloalkenyl, C$_3$–C$_{12}$heterocycloalkyl-C$_1$–C$_6$alkyl, C$_3$–C$_{12}$heterocycloalkenyl-C$_1$–C$_6$alkyl, C$_4$–C$_{18}$heteroaryl, C$_5$–C$_{18}$heteroalkyl, each of which is bonded via a C atom and has hetero atoms selected from the group of O, S and N;

R$_5$ is —CN or a —C(=O)—R$_7$ group;

R$_6$ independently has the same meanings as R$_4$ or is linear or branched C$_1$–C$_{18}$alkoxy, C$_3$–C$_{12}$cycloalkoxy, C$_3$–C$_{12}$cycloalkyl-C$_1$–C$_6$alkoxy, C$_6$–C$_{18}$aryloxy, C$_7$–C$_{18}$aralkyloxy, C$_3$–C$_{12}$heterocycloalkyloxy, C$_3$–C$_{12}$heterocycloalkyl-C$_1$–C$_6$alkyloxy, C$_4$–C$_{18}$heteroaryloxy, C$_5$–C$_{18}$heteroaralkyl having hetero atoms selected from the group of O, S and N;

R$_7$ is linear or branched C$_1$–C$_{18}$alkyl, C$_2$–C$_{18}$alkenyl, C$_3$–C$_{12}$cycloalkyl, C$_3$–C$_{12}$cycloalkenyl, C$_3$–C$_{12}$cycloalkyl-C$_1$–C$_6$alkyl, C$_3$–C$_{12}$cycloalkenyl-C$_1$–C$_6$alkyl, C$_6$–C$_{18}$aryl, C$_7$–C$_{18}$aralkyl, or C$_3$–C$_{12}$heterocycloalkyl, C$_3$–C$_{12}$heterocycloalkenyl, C$_3$–C$_{12}$heterocycloalkyl-C$_1$–C$_6$alkyl, C$_3$–C$_{12}$heterocycloalkenyl-C$_1$–C$_6$alkyl, C$_4$–C$_{18}$heteroaryl, C$_5$–C$_{18}$heteroalkyl, each of which is bonded via a C atom and has hetero atoms selected from the group of O, S and N, linear or branched C$_1$–C$_{18}$alkoxy, C$_3$–C$_{12}$cycloalkoxy, C$_3$–C$_{12}$cycloalkyl-C$_1$–C$_6$alkoxy, C$_6$–C$_{18}$aryloxy, C$_7$–C$_{18}$aralkyloxy, C$_3$–C$_{12}$heterocycloalkyloxy, C$_3$–C$_{12}$heterocycloalkyl-C$_1$–C$_6$alkyloxy, C$_4$–C$_{18}$heteroaryloxy, C$_5$–C$_{18}$heteroaralkyl having hetero atoms selected from the group of O, S and N;

R$_4$ and R$_6$ together with the group —C—C(=O)— to which they are bonded are an aliphatic or heteroaromatic, saturated or unsaturated, single or polycyclic ring which contains 3 to 18 ring members and to which aromatic or heteroaromatic rings may be fused;

R$_6$ and R$_7$ together with the group —(O=)C—C—C(=O)— to which they are bonded are an aliphatic or heteroaromatic, saturated or unsaturated, single or polycyclic ring which contains 3 to 18 ring members and to which aromatic or heteroaromatic rings may be fused;

where R$_4$, R$_5$, R$_6$ and R$_7$ are unsubstituted or substituted as defined above for methylene and methine compounds.

4. The process according to claim 1, wherein the halogenation reagent is a fluorination reagent selected from the group of inert gas fluorides, fluoroalkoxyfluorides, sulfonyl fluorides, N-fluorinated pyridinium salts, tertiary N-fluoroammonium salts, N-fluorinated amides and imides, $FClO_3$, and $F_2$.

5. The process according to claim 4, wherein the fluorination reagent is selected from the group of xenon difluoride, $(CF_3)_2CFOF$, $CF_3SO_2F$, N-fluorinated internal salts of pyridines and bipyridyls substituted by sulfo groups, triflates or tetrafluoroborates of N-fluorinated pyridines and bipyridyls, N-alkylated and N-fluorinated sulfonamides, carboxamides, lactams and sultams, N-fluorinated dicarboximides and disulfonimides.

6. The process according to claim 4, wherein the fluorination reagent is a 1-substituted 4-fluoro-1,4-diazoniabicyclo[2,2,2]octane salt with complex anions and substituents selected from $C_1$–$C_4$alkyl, $C_1$–$C_4$hydroxyalkyl and $C_1$–$C_4$haloalkyl.

7. The process according to claim 6, wherein the fluorination reagent is 1-chloromethyl- or 1-hydroxymethyl-4-fluoro-1,4-diazoniabicyclo[2,2,2]octane bistetraf luoroborate.

8. The process according to claim 1, wherein the halogenation reagent for the chlorination, bromination and iodination is selected from the group of $C_{12}$, $Br_2$, $I_2$, N-chlorinated, N-brominated and N-iodinated dicarboximides or disulfonimides, lactams and sultams, N-alkyl- or N-phenylcarboxamides or -sulfonamides, dialkylamines or monoalkylamines.

9. The process according to claim 8, wherein the halogenation reagent is N-chloro-, N-bromo- or N-iodosuccinimide.

10. The process according to claim 1, wherein the titanium compounds of the formula I are titanium tetrachloride, titanium tetrabromide, cyclopentandienyltitanium trichloride and cyclopentadienyltitanium tribromide.

11. The process according to claim 1, wherein $X_1$ and $X_2$ in formula II are bromine or chlorine.

12. The process according to claim 1, wherein the diolates are divalent radicals of diols whose hydroxyl groups are bonded in the 1,3, 1,4 or 1,5 positions of a substituted or unsubstituted $C_3$, $C_4$ or $C_5$ chain in an open-chain, cyclic or cyclic-aliphatic compound, and substituents selected from the group of halogen, $C_1$–$C_8$alkyl, $C_3$–$C_8$cycloalkyl, $C_3$–$C_8$cycloalkyl-$C_1$–$C_4$alkyl, $C_6$–$C_{10}$aryl, $C_7$–$C_{12}$aralkyl, and, bonded in the 2 and/or 3 position, $C_1$–$C_8$alkoxy, $C_3$–$C_8$cycloalkoxy, $C_3$–$C_8$cycloalkyl-$C_1$–$C_4$alkoxy, $C_6$–$C_{10}$aryloxy, $C_7$–$C_{12}$aralkyloxy, or, bonded in the 2,3 position and unsubstituted or substituted by a hydrocarbon radical as defined above, trimethylene, tetramethylene, ethylene-1,2-dioxy or methylenedioxy, where cyclic substituents in turn are unsubstituted or substituted by $C_1$–$C_4$alkyl, $C_1$–$C_4$alkoxy or halogen.

13. The process according to claim 12, wherein the diolates are 1,4-diolates including 1,1' bicyclic hydrocarbons with hydroxyl groups bonded in the 2,2' position.

14. The process according to claim 12, wherein the butane-1,4-diolates have the formula VII

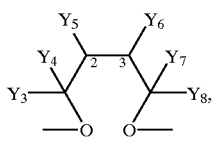

(VII)

in which
$Y_3$, $Y_4$, $Y_5$, $Y_6$, $Y_7$ and $Y_8$ are, independently of one another, a hydrogen atom, $C_1$–$C_8$alkyl and preferably $C_1$–$C_4$alkyl, $C_3$–$C_8$cycloalkyl and preferably $C_5$–$C_6$cycloalkyl, $C_3$–$C_8$cycloalkyl-$C_1$–$C_4$alkyl and preferably $C_5$–$C_6$cycloalkylmethyl or -ethyl, $C_6$–$C_{10}$aryl and preferably phenyl or naphthyl, $C_7$–$C_{12}$aralkyl and preferably benzyl and phenylethyl;

$Y_5$ and $Y_6$ are $C_1$–$C_8$alkoxy and preferably $C_1$–$C_4$alkoxy, $C_3$–$C_8$cycloalkoxy and preferably $C_5$–$C_6$cycloalkoxy, $C_3$–$C_8$cycloalkyl-$C_1$–$C_4$alkoxy and preferably $C_5$–$C_6$cycloalkylmethoxy or -ethoxy, $C_6$–$C_{10}$aryloxy and preferably phenyloxy or naphthyloxy, $C_7$–$C_{12}$aralkyloxy and preferably benzyloxy and phenylethyloxy;

$Y_5$ and $Y_6$ are, together with the C atoms to which they are bonded, $C_5$–$C_8$cycloalkyl; or $Y_5$ and $Y_6$ are together with the C atoms to which they are bonded, the radical —O—$CY_9Y_{10}$—O—;

$Y_9$ and $Y_{10}$ are, independently of one another, a hydrogen atom, $C_1$–$C_8$alkyl and preferably $C_1$–$C_4$alkyl, $C_3$–$C_8$cycloalkyl and preferably $C_5$–$C_6$cycloalkyl, $C_3$–$C_8$cycloalkyl-$C_1$–$C_4$alkyl and preferably $C_5$–$C_6$cycloalkylmethyl or -ethyl, $C_6$–$C_{10}$aryl and preferably phenyl or naphthyl, $C_7$–$C_{12}$aralkyl and preferably benzyl and phenylethyl;

$Y_3$, $Y_4$, $Y_5$, $Y_6$, $Y_7$, $Y_8$, $Y_9$ and $Y_{10}$ are unsubstituted or substituted by halogen, $C_1$–$C_4$alkyl or $C_1$–$C_4$alkoxy;

with the proviso that at least one of $Y_3$, $Y_4$, $Y_5$, $Y_6$, $Y_7$, $Y_8$, $Y_9$ and $Y_{10}$ is one of said radicals.

15. The process according to claim 14, wherein $Y_5$ and $Y_6$ in formula VII are, together with the C atoms to which they are bonded, $C_5$–$C_8$cycloalkyl or the radical —O—$CY_9Y_{10}$—O—.

16. The process according to claim 1, which is enantioselective through use of compounds of the formula II in which $R_2$ and $R_3$ are an enantiopure 1,3-, 1,4- or 1,5-diolate as catalysts for reacting activated racemic methine compounds.

17. The process according to claim 16, wherein the enantiopure diolate has the formula VII according to claim 14, or the formulae V, VI

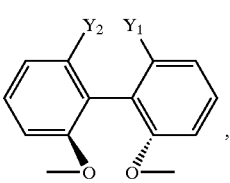

(V)

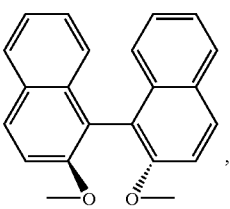

(VI)

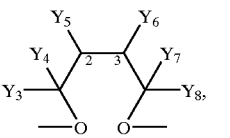

(VII)

in which $Y_1$ and $Y_2$ are $C_1$–$C_4$alkyl, $C_1$–$C_4$alkoxy or halogen, and no or 5- or 6-membered carbocyclic rings are fused to the benzene rings, or have the formulae

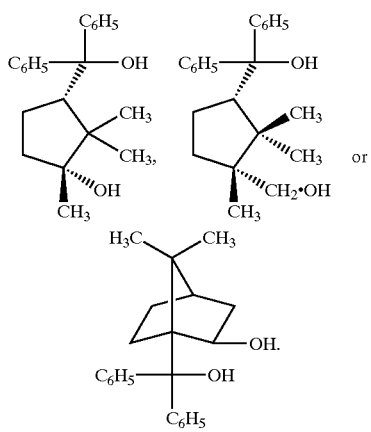

18. The process according to claim 16, wherein the enantiopure diolate is (4R,5R)- and (4S,5S)-4,5-bis(diphenylhydroxymethyl)-2,2-dimethyldioxolane or (4R,5R)- and (4S,5S)-4,5-bis(di-1-naphthylhydroxymethyl)-2,2-dimethyidioxolane.

19. The process according to claim 1, wherein the catalyst is employed in an amount of 0.5 to 20 mol % based on the activated methylene or methine compounds.

20. The process according to claim 1, which is carried out at a temperature of from −40 to 120° C.

21. The process according to claim 13, wherein the 1,4-diolate is a 1,1' bicyclic hydrocarbon with hydroxyl groups bonded in the 2,2' positions.

22. The process according to claim 14, wherein $Y_3$, $Y_4$, $Y_5$, $Y_6$, $Y_7$ and $Y_8$ are, independently of one another, $C_1$–$C_4$alkyl, $C_5$–$C_6$cycloalkyl, $C_5$–$C_6$cycloalkylmethyl or -ethyl, phenyl, napthyl, benzyl or phenylethyl;

$Y_5$ and $Y_6$ are $C_1$–$C_4$alkoxy, $C_5$–$C_6$cycloalkoxy, $C_5$–$C_6$cycloalkylmethoxy or -ethoxy, phenyloxy, napthyloxy, benzyloxy or phenylethloxy;

$Y_9$ and $Y_{10}$ are, independently of one another, $C_1$–$C_4$alkyl, $C_5$–$C_6$cycloalkyl, $C_5$–$C_6$cycloalkylmethyl or -ethyl, phenyl, naphthyl, benzyl or phenylethyl.

23. The process according to claim 17, wherein $Y_3$, $Y_4$, $Y_5$, $Y_6$, $Y_7$ and $Y_8$ are, independently of one another, $C_1$–$C_4$alkyl, $C_5$–$C_6$cycloalkyl, $C_5$–$C_6$cycloalkylmethyl or -ethyl, phenyl, napthyl, benzyl or phenylethyl;

$Y_5$ and $Y_6$ are $C_1$–$C_4$alkoxy, $C_5$–$C_6$cycloalkoxy, $C_5$–$C_6$cycloalkylmethoxy or -ethoxy, phenyloxy, napthyloxy, benzyloxy or phenylethloxy;

$Y_9$ and $Y_{10}$ are, independently of one another, $C_1$–$C_4$alkyl, $C_5$–$C_6$cycloalkyl, $C_5$–$C_6$cycloalkylmethyl or -ethyl, phenyl, naphthyl, benzyl or phenylethyl.

* * * * *